United States Patent
Bogen et al.

(10) Patent No.: US 6,281,004 B1
(45) Date of Patent: Aug. 28, 2001

(54) QUALITY CONTROL FOR CYTOCHEMICAL ASSAYS

(75) Inventors: Steven A. Bogen, Sharon; Gail E. Radcliffe, Worcester, both of MA (US)

(73) Assignee: Cytologix Corporation, Cambridge, MA (US)

( * ) Notice: Subject to any disclaimer, the term of this patent is extended or adjusted under 35 U.S.C. 154(b) by 0 days.

(21) Appl. No.: 09/291,351

(22) Filed: Apr. 14, 1999

(51) Int. Cl.[7] .................. G01N 33/543; G01N 33/553; G01N 33/569
(52) U.S. Cl. .................. 435/287.1; 422/56; 422/57; 422/58; 422/59; 422/60; 422/61; 435/6; 435/7.1; 435/7.21; 435/7.23; 435/7.24; 435/960; 435/7.9; 435/7.92; 435/7.93; 435/7.94; 435/287.1; 436/512; 436/513; 436/518; 436/519; 436/527; 436/531; 436/532; 436/543; 436/546; 436/548; 436/8; 436/63; 436/64; 436/809; 436/810; 536/24.3
(58) Field of Search .................. 435/6, 7, 7.1, 7.21, 435/7.23, 7.24, 91.2, 960, 967, 7.9, 7.92, 7.93, 7.94, 287.1, 291; 436/501, 518, 519, 527, 531, 532, 543, 546, 548, 8, 63, 64, 174, 176, 178, 805, 809, 819, 823, 512, 513, 525, 169; 422/56, 57, 58, 59, 60, 61; 536/24.3

(56) References Cited

U.S. PATENT DOCUMENTS

| | | | |
|---|---|---|---|
| 4,591,570 | * | 5/1986 | Chang .................. 436/518 |
| 4,715,988 | | 12/1987 | Colin .................. 252/408.1 |
| 4,820,504 | | 4/1989 | Battifora .................. 424/3 |
| 4,914,022 | | 4/1990 | Furmanski et al. .................. 435/7 |
| 5,143,714 | | 9/1992 | Cosgrove et al. .................. 424/3 |
| 5,223,409 | | 6/1993 | Ladner et al. .................. 435/69.7 |
| 5,501,954 | * | 3/1996 | Mahr et al. .................. 435/6 |
| 5,541,059 | | 7/1996 | Chu .................. 435/5 |
| 5,571,698 | | 11/1996 | Ladner et al. .................. 435/69.7 |
| 5,610,022 | | 3/1997 | Battifora .................. 435/7.23 |
| 5,837,500 | | 11/1998 | Ladner et al. .................. 435/69.7 |
| 5,846,749 | | 12/1998 | Slamon et al. .................. 435/7.23 |
| 5,879,951 | | 3/1999 | Sy .................. 436/514 |
| 5,885,526 | * | 3/1999 | Chu .................. 422/56 |

FOREIGN PATENT DOCUMENTS

| | | |
|---|---|---|
| 0 266 077 B1 | 10/1987 | (EP) . |
| 0 345 953 A2 | 5/1989 | (EP) . |
| 90/02809 | 3/1990 | (WO) . |
| WO 91/05263 | 4/1991 | (WO) . |

OTHER PUBLICATIONS

Nibbering, P.H. and VanFurth, R., "Microphotmetric Quantitation of the Reaction Product of Several Indirect Immunoperoxidase Methods Demonstrating Monoclonal Antibody Binding to Antigens Immobilized on Nictrocellulose," *J. of Histochemistry and Cytochemistry*, 34(12):1425–1431 (1987).

Gagne, G.D. and Miller, M.F., "An Artificial Test Substrate for Evaluating Electron Microscopic Immunocytochemical Labeling Reactions," *J. of Histochemistry and Cytochemistry*, 35(8):909–916 (1987).

(List continued on next page.)

Primary Examiner—Long V. Le
Assistant Examiner—Gailene R. Gabel
(74) Attorney, Agent, or Firm—Hamilton, Brook, Smith & Reynolds, P.C.

(57) ABSTRACT

The invention describes quality control devices for assays that measure analytes in cells and tissue samples, and methods of use thereof. In particular, the quality control device comprises a matrix affixed with synthetic controls in different concentrations, or different synthetic controls. The quality control device can be adhered to a microscope slide and processed simultaneously with a tissue sample.

42 Claims, 4 Drawing Sheets

OTHER PUBLICATIONS

Hough, T., et al., "Immunofluorescent Screning of Monoclonal Antibodies to Surface Antigens of Animal and Plant Cells Bound to Polycarbonate Membranes," *J. Immunological Methods*, 92:103–107 (1986).

Nabors, L.B., et al., "Quantitative Immunocytochemistry Using an Image Analyzer. II. Concentration Standards for Transmitter Immunocytochemistry," *J. Neuroscience Methods*, 26:25–34 (1988).

Riera, J., et al., "Use of Cultured Cells as a Control for Quantitative Immunocytochemical Analysis of Estrogen Receptor in Breast Cancer," *Am J. Clin Path*, 111:329–335 (1999).

Bon, G.G., et al., "Clinical and Technical Evaluation of ACS BR Serum Assay of MUCI Gene–Derived Glycoportein in Breast Cancer, and Comparison with CA15–3 Assays," *Clin. Chem.*, 43:585–593 (1997).

Wells, J. and Lowman, H., *Curr. Op. Struct, Biol.*, 3(4):355–362 (1992).

McLafferty, M., et al., *Gene*, 128:29–36 (1993).

Clackson, T. and Wells, J., *TIBTECH*, 12:173–184 (1994).

Roberts, B., et al., *Proc. Natol. Acad. Sci. USA*, 89:2429–2433 (1992).

Markland, W., et al., *Biochemistry*, 35:8058–8067 (1996).

Markland, et al., *Biochemistry*, 35:8045–8057 (1996).

Ley, A., et al., *Mol. Divers.*, 2:119–124 (1996).

\* cited by examiner

QUALITY CONTROL FOR CYTOCHEMICAL ASSAYS

BACKGROUND OF THE INVENTION

During the past decade, immunohistochemical (IHC) stains have become an integral part of the diagnostic process in surgical pathology. IHC stains are used with conventional histopathological stains, as adjunctive assays. They are critical in correctly diagnosing poorly differentiated malignancies, viral infections, and tumor prognoses, such as in the use of estrogen receptor (ER) analysis for breast carcinoma. Since IHC assays are relatively new in medical practice, a method for accurately and reliably monitoring quality control has not yet been developed.

Traditional microscopic analysis of biopsy samples demonstrates overall cellular and tissue architecture. With the commonly used hematoxylin and eosin stain, for example, nuclei are colored purple (with hematoxylin) and the cytoplasm red/pink (with eosin). Often, the type of information available from such stains is insufficient for accurate diagnosis. IHC stains have the ability to extend the level of analysis on a biopsy sample, beyond cellular size and shape, to a molecular level. Tissue samples can be probed for the presence of specific proteins using monoclonal and polyclonal antibodies. The presence of such proteins can be indicative of the cellular lineage of a tumor, facilitating a diagnosis or prognosis with certain types of anti-tumor therapies. Alternatively, the presence of microbiologic agents, such as viruses or bacteria, can be detected using appropriate antibodies.

Quality control is an important aspect of any clinical assay. To assure that clinical test results are accurate, controls should be run with all in vitro diagnostic tests. Quality control in the clinical laboratory is mandated by the Clinical Laboratory Improvement Act of 1988 (CLIA '88). This act outlines the regulatory requirements that a clinical laboratory must meet in order to obtain accreditation; controls and proficiency testing comprise a significant portion of the act. Many tests in the hematology and chemistry sections of the laboratory include controls that are provided by the manufacturer. In contrast, most histology laboratories generate their own controls from excess tissue specimens. With laboratories generating their own control tissues, there is little inter-laboratory standardization. The need for better quality control of immunoreagents was recognized in the late 1980's and led to workshops convened by the Biological Stain Commission to address the issue.

The histology laboratory has lagged behind other sections of the clinical laboratory in the implementation of optimal controls. A negative control is easy to perform. It comprises a serial section of the same tissue with an irrelevant, isotype-matched primary antibody. Standardized positive controls have been harder to achieve. Presently, each laboratory is left to fend for itself in creating, storing, and validating positive tissue controls.

Most histopathology laboratories use tissue samples previously documented to contain the particular antigen as positive controls. The laboratory documents, sections, and archives a bank of tissues that will serve as tissue controls for IHC. As the tissue controls are depleted, new tissues/tumor samples are procured to replace those expended. During each daily IHC assay run, each antibody is tested on a positive tissue control. In this manner, each antibody is validated at a specified dilution.

An improvement was described by Battifora (U.S. Pat. Nos. 4,820,504 and 5,610,022) whereby multiple positive control tissue fragments, often of tumors, are embedded together in a single paraffin block. This "multi-tissue tumor block" simplifies the sectioning process of positive tissue controls. Rather than archiving and sectioning numerous blocks of tissue, the tissue controls are embedded together in a single paraffin block. Therefore, the group of archived tissues can be sectioned simultaneously, with a single stroke of a microtome blade.

A slightly simpler method of preparing multi-tumor tissue paraffin blocks was described by Furmanski et al. (U.S. Pat. No. 4,914,022). The improvement involved embedding tissue cores in a paraffin block. The cores were cut from the tissue of origin with the use of an ordinary plastic drinking straw.

The use of multi-tumor tissue blocks as positive controls does not solve three important problems. One of the most important aspects that a positive control should address is the early detection of reagent failure. The ideal method of detecting early failure is to determine the level of sensitivity at the working concentration of antibody. Sensitivity is determined by titrating the antigen concentration until the antigen is no longer detected. In this manner, the assay can be stated as capable of detecting a certain amount of antigen, e.g., nanomoles or picomoles of antigen. The limit of sensitivity should ideally be checked daily so that trends (towards increasing or decreasing sensitivity) can be detected. It is impossible to perform this type of analysis using tissue sections as controls, since there is no practical method for quantitation and titration of antigen in a tissue section.

In addition, tissue sections as controls do not control for performance error. Cutting (with a microtome) and mounting tissue sections on glass slides is labor intensive. Therefore, the aforementioned types of tissue positive controls (such as multi-tumor tissue blocks) are usually tested once per assay run. Because of the associated labor costs, few laboratories place a positive tissue control on each microscope slide. Thus, if there is an error by placing an incorrect antibody (or no antibody) on the sample, it may be impossible to detect. Importantly, the control slide may be correctly treated (verifying the reagent quality) but the sample slide can still be incorrectly treated. The sample would therefore be interpreted as a negative result, although the cause of the negative result is an error in the assay procedure. The present system of positive tissue controls does not control for errors in procedure.

A third problem with tissue sections as positive IHC assay controls is that tumor tissues inherently have a varied, non-standardized amount of antigen. Therefore, tissues do not provide a ready means for calibrating the intensity of the immunologic reaction to an external reference standard. For certain IHC assays, the absence of external reference calibrators is a serious problem. Notably, IHC assays for estrogen receptor and progesterone receptor have become the gold standard for previously quantitative assays that were performed in a test tube. In the absence of such calibrators, staining is typically quantified as 0–4+ staining intensity, an arbitrary standard that depends upon the reagents, protocol, and time duration of calorimetric development. Because of significant inter-laboratory variability in IHC assay sensitivity, each hospital laboratory must develop its own threshold for determining a positive result. This feature leads to non-standard and sometimes incorrect results. These errors can have therapeutic impact on patient care.

Therefore, a standardized, practical positive tissue control for clinical IHC assays should have the following characteristics to be clinically accepted and scientifically meaningful:

1. Antigen specific. A positive reaction should indicate the presence of only the antigen being assayed.
2. Available in virtually unlimited quantities, so that the positive control has constantly controlled characteristics with the passage of years.
3. Inexpensive. With cost pressures mounting on hospital laboratories, an expensive positive control will most likely not be broadly adopted into routine practice.
4. Stable over a prolonged period of time, ideally without the need for freezing.
5. Standardized, so that each laboratory will have the exact same positive control substrate.

Currently, there is not a quality control reagent or device available for cytotochemical procedures that has all of the above characteristics.

SUMMARY OF THE INVENTION

The present invention relates to the development of an accurate, reliable and easy-to-use quality control device, and methods of using that device, to maintain quality control of assays that measure analytes in cells or tissue sections, specifically immunohistochemical analyses of biological samples. As used herein, the term "biological sample" can be any cell-containing sample. For example, the sample can be tissue, blood, urine, cerebral spinal fluid (CSF), sputum, semen, cervicovaginal swab, or intestinal wash. For example, the analyte assay can be an immunocytochemical assay and the target molecule (analyte) to be detected is an antigen. As used herein, the term "antigen" means a molecule detected by an antibody.

Specifically, the present invention relates to a quality control device comprising one, or more, quality control moieties which are affixed to a reagent surface of a matrix. Each moiety is confined to a discrete section, or "spot" on the matrix. Typically, the moieties are covalently attached to the matrix. The quality control moiety comprises one, or more, target molecules (e.g., the molecule of interest that is being detected in the biological sample) or a target molecule mimic (e.g., synthetic molecule that mimics the target molecule). Typically the target molecule is a protein (e.g., a native protein, or an antibody such as a goat anti-mouse immunoglobulin antibody) or polypeptide (e.g., synthetic protein or antibody fragment) that is detectable by antibody binding. Other target molecules are proteins or polypeptides, carbohydrates, lipids, or combinations thereof that are detectable by histochemical stains. Representative histochemical stains include the periodic acid-schiff stain, mucicarmine stain or reticulin stain. Target molecules can also be nucleic acids (e.g., that are detectable by in situt hybridization techniques). For example, in this embodiment, the target is a nucleic acid detected by a nucleic acid probe complementary to the nucleotide sequence of the target molecule.

In one embodiment, the target molecule is an protein, polypeptide, or fragment thereof, that is detectable by a specific antibody (referred to herein as the primary antibody). The primary antibodies of the present invention can be either polyclonal or monoclonal, but are typically monoclonal. Such proteins, polypeptides or fragments (e.g., small peptides) are referred to herein as antigens. Antigens for use in the quality control device described herein can be purified antigens, recombinantly produced antigens or synthetic antigens. In order to simplify manufacture, it is desirable to avoid the need for purification of the many different antigens that are used in clinical diagnosis. Therefore, a preferred form of the antigen of the quality control device described herein is a synthetic, short peptide sequence that mimics the antigen to be detected and specifically binds to the primary antibody under substantially the same conditions as the antigen to be detected.

In this embodiment of the present invention, antigen is affixed to the quality control device, for example, by placing a small spot of soluble antigen (i.e., antigen in a suitable solution, such as a buffered saline solution) onto a spatially discrete region, or section, of the matrix. The matrix can be any material suitable for permanently affixing the antigen. Preferably, a series of spots, each with soluble antigen in varying concentrations, are placed onto the matrix. In this way, the immunologic reaction on the matrix will cause some spots to be intensely colored and others not at all. For example, to determine the sensitivity of an immunocytochemical assay, the endpoint of detection is determined as the spot of lowest antigen concentration that still produces a 1+ intensity (on a 0–4+ scale). In this manner the sensitivity of the assay and initial stages of reagent failure can be determined. In addition, an irrelevant antigen can also applied to the matrix as a check for reaction specificity.

Alternatively, different antigens can be affixed to the matrix in order to detect multiple distinct primary antibodies. In this alternative embodiment, the quality control invention would be more versatile, in that it would provide an antigen-specific binding site for multiple different primary antibodies.

In another embodiment of the present invention, the quality control moiety is an antibody that recognizes the primary antibody that binds to the target molecule. For example, the quality control moiety can be goat anti-mouse immunoglobulin (IgG) if the primary antibody is a mouse antibody, or rabbit anti-human antibody, if the primary antibody is a human antibody. In this embodiment, the quality control device monitors for the presence of primary antibody and whether immunocytochemical reagents used during the cytochemical assay (e.g., second antibody or enzyme) are applied in the correct sequential order.

In one embodiment of the present invention, the quality control device is an adhesive device wherein the matrix of the device has a front and back surface. The front surface is referred to herein as the reagent surface and has one, or more, quality control moieties affixed to the surface. The back surface of the matrix is referred to herein as the adhesive surface, which permits the quality control device to be affixed to a test platform. The test platform can be a flat, optically transparent surface, for example, a microscope slide. For simplicity, the quality control device is often referred to herein as a "strip" of matrix material, however, it is readily apparent that other shapes, or forms of the matrix can be used in the device of the present invention, and these alternative forms are also encompassed by the present invention. For example, the quality control device comprising an adhesive matrix strip can be peeled from a backing and applied to the end of a microscope slide. The biological sample (e.g., tissue section) to be tested is also affixed to the same microscope slide. Therefore, the same reagents, temperature, and humidity conditions that exist for the cytochemical reaction on the tissue section also apply to the synthetic antigen control moieties affixed to the device.

Methods of using the devices described herein are also encompassed by the present invention. For example, encompassed by the present invention are methods for determining the sensitivity of an assay for the detection of the presence or absence of one, or more, target molecules in a biological sample. The method comprises simultaneously processing the biological sample and a quality control device described herein in the assay to detect the presence or absence of one, or more target molecules. As used herein the term "processing" means performing all the steps of an assay required to detect the presence, or absence, of the target molecule. For example, processing can mean performing the steps of an immunocytochemical assay to detect the presence of a target protein by contacting the protein with an antibody that specifically binds to the protein, under appropriate conditions wherein the antibody specifically binds to the target protein and detecting the antibody bound to the target (e.g., by detecting a colorimetric signal) wherein detection of the signal is indicative of the presence of the target protein, and lack of signal detection is indicative of the absence of the target protein. Such assay steps are well-known to those of skill in the art. For example, the device can comprise a matrix with quality control moieties with different concentrations of a target molecule or target molecule mimic, e.g., a synthetic antigen, which is covalently attached to the matrix. The synthetic antigen mimics the antigenic site of the target molecule and thus is also recognized by same antibody that recognizes the target molecule. The processing results in the detection of target molecule in the sample and target molecule or target molecule mimic in the quality control moiety of the device using one of the detection methods described herein. The moiety that contains the lowest concentration of target molecule/target molecule mimic is then determined, wherein determination of the lowest concentration of detectable target molecule/target molecule mimic is indicative of the sensitivity of the immunocytochemical assay. Typically, the device is affixed to a flat, optically transparent surface, e.g., a microscope slide.

Also encompassed by the present invention is an immunocytochemical assay method for validating, or verifying, the proper performance of the assay, for example, an assay that detects the presence or absence of a target molecule in a biological sample. The method comprises simultaneously processing the biological sample and a quality control device in the assay, wherein processing results in a detectable signal (e.g., a calorimetric signal) produced by the target molecule and by the quality control reagent moiety. As described above, the processing results in the detection of the signal, therefore detection of the target molecule in the biological sample and the target molecule/target molecule mimic in the quality control reagent moiety. As described above, the quality control moiety can be a synthetic antigen/ target molecule mimic. The fact that the quality control reagent moiety develops a calorimetric signal provides independent validation that the assay on the biological sample was executed correctly. This is especially important in instances where the biological sample yields a negative result, i.e., no color development. The fact that the quality control strip yielded a positive reaction establishes that the result is a true negative and not due to errors in the procedure or problems with reagent quality. Thus validation is established because the biological sample and the quality control device are typically affixed to the same microscope slide. Therefore, both the tissue sample and the quality control device contacted the same series of reagents, for the same time and temperature.

Another method of the present invention encompasses an assay method (e.g, an immunocytochemical assay) for the determination of the concentration of a target molecule in a biological sample. The method comprises simultaneously processing the biological sample and a quality control device in the immunocytochemical assay as described above. The processing results in a detectable signal generated by the presence of the target molecule in the biological sample and target molecule/target molecule mimic in the quality control moiety. The detectable signal generated from the target molecule in the biological sample is compared with the detectable signal generated from the target molecule (or synthetic antigen mimic) in the quality control reagent moiety to determine the concentration of target molecule in the biological sample.

As a result of the invention described herein, quality control devices and methods are now available to serve as a quality control tool to verify that a cytochemical, immunocytochemical, or in situ hybridization procedure was executed correctly. Use of the quality control device of the present invention verifies that each and every tissue sample received the correct reagents, in the proper sequence and timing, leading to proper staining. Moreover, it verifies the integrity of the reagents.

DETAILED DESCRIPTION OF THE INVENTION

Figure 1:
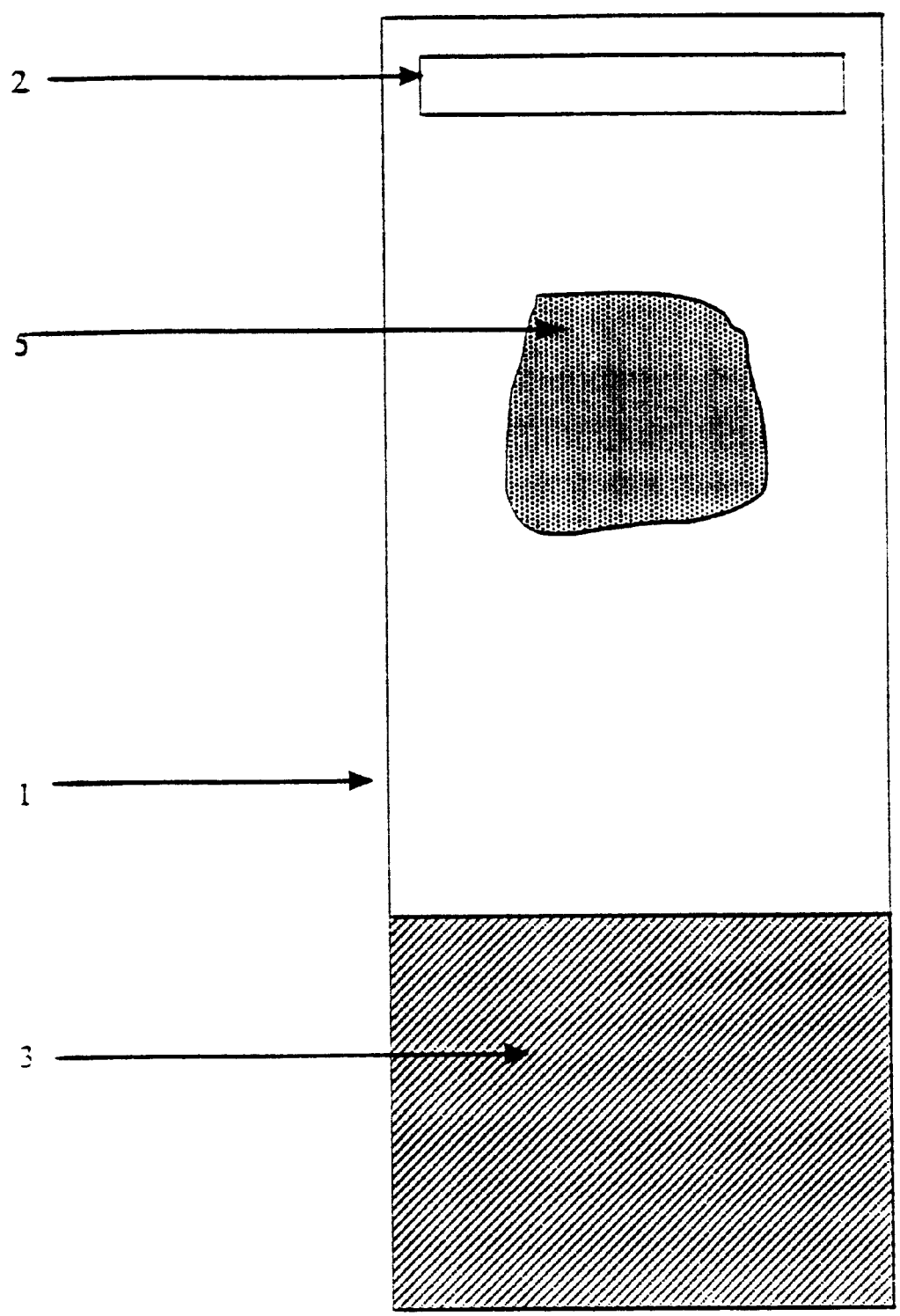
FIG. 1 is an en face view of a microscope slide with a patient label and patient tissue sample. Additionally, the drawing demonstrates where on the slide the adhesive antigen strip might be positioned.

The present invention as herein described addresses the important quality control issues in cytochemical assays, and in particular in immunohistochemical (IHC) assays. Most histopathology laboratories use tissue samples previously documented to contain particular antigens of interest (target antigen) as positive controls.

One of the most important aspects that a positive control should address is the early detection of reagent failure. The ideal method of detecting early failure is to determine the level of sensitivity of the working concentration of antibody. Sensitivity is determined by titrating the antigen concentration until the antigen is no longer detected. In this manner, the sensitivity of the assay can be stated as the limit of the assay to detect a certain amount of antigen, e.g., nanomoles or picomoles of antigen. The limit of sensitivity should ideally be checked daily. In this manner, long-term trends (towards decreasing or increasing sensitivity) can be detected. It is impossible to perform this type of analysis using tissue sections, since there is no practical method for quantitation and titration of antigen in a tissue section.

Immunohistochemical assays are inherently more prone to operator performance error than conventional immunoassays. This creates an additional problem with the existing systems of quality control. Namely, even if the control tissue slide appears satisfactory, how is a performance error detected on another (sample) slide?

There are several reasons that IHC assays are predisposed to operator error. First, the fact that the IHC reaction is performed on a microscope slide—a flat planar surface— allows for the possibility that the reagent may fall off the edge of the slide or evaporate, which would result in unsatisfactory staining due to tissue drying. Conventional immunoassays, performed in test tubes, cuvettes, microwells, or the like, have supporting walls for the reagent. This physical constraint for the reagent prevents reagent spillage.

Additionally, many clinical laboratories still perform IHC staining manually. This inherently creates the possibility that the technologist can place an incorrect reagent, or no reagent, during one of the many steps in the procedure.

Even with an automated platform, which are recently gaining market acceptance, machine malfunction is reported on an anecdotal level. Each of the machine platforms assumes that an electromechanical action translates into a dispensed volume of reagent. This is not always the case. For example, an automatic reagent dispenser can have several potential failure modes. These include insufficient priming of the dispenser, a leaking dispenser due to a faulty seal, and excessive friction (creating a drag force) by the plunger in the reagent reservoir. Standard XYZ axis pipettors depend upon the technician placing a sufficient amount of antibody into a vial at the beginning of each run.

The final step in IHC staining is colorimetric development, catalyzed by an enzyme such as peroxidase or alkaline phosphatase. A colorless and soluble substrate is converted into a colored and insoluble precipitate. The timing of the reaction is important. Too short a development yields a poor signal while too long a development time can increase non-specific background staining. Consequently, this step is performed under the watchful eye of the technologist, who examines the tissue sections for color development under the microscope. When the color is optimally developed, with low background, the technologist stops the reaction by immersing the slide in buffer. In practice, this step is labor-intensive, since each slide is examined individually.

The use of a quality control device with every assay, or on every microscope slide, would solve the assay performance problem. Described herein is a quality control device comprising multiple quality control reagent moieties affixed to a matrix or membrane. The quality control device can be affixed, or adhered, to a test platform, such as a microscope slide, using an adhesive. These reagent moieties comprise the target molecule (e.g., the antigen, antibody or nucleic acid to be detected in the assay), or a target molecule mimic, defined herein as a molecule that mimics the characteristics, or properties (e.g., physical structure or antigenic properties) of the target molecule sufficiently so that the mimic molecule reacts substantially the same as the target molecule in the cytochemical assay. In one embodiment of the present invention, the target molecule mimic is a short synthetic peptide the mimics the antigen site of the target molecule and therefore, binds to antibody specific for the target molecule (also referred to herein as a synthetic antigen or synthetic control).

In one embodiment of the present invention, the quality control device comprises a membrane strip, approximately 0.8×0.2 inches, with an adhesive backing that can be applied to a microscope slide. FIG. 1 demonstrates a recommended position on the microscope slide (1) for such a control strip (2). At one end, a label (3) with patient information is typically applied. The information on the label typically includes the type of stain, surgical accession number, patient name, and occasionally a bar code. The tissue section (5) is typically placed in the middle of the slide. Immunohistochemical reactions are performed by the sequential incubation and removal of a series of reagents to and from the tissue section (5). By placing the control strip (2) near the tissue section (5), the strip will also contact the same reagents, as they are applied and removed.

Figure 2:
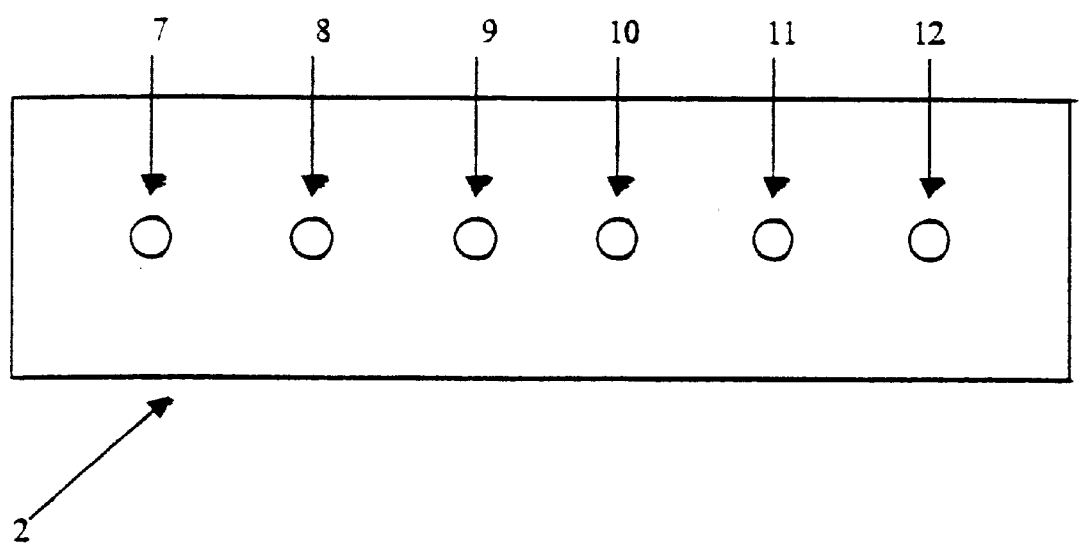
FIG. 2 is an en face view of the antigen strip showing the positions of the antigen spots.

FIG. 2 demonstrates the placement of antigen on a representative antigen control strip. A series of spots of antigen (7–12) are evenly spaced across the length of the strip. Each spot comprises a macromolecule, preferably a peptide, immobilized onto the membrane matrix. In a preferred embodiment, spots 8–12 comprise the same peptide at different molar concentrations immobilized onto the membrane matrix. Therefore, if an inmmunohistochemical assay is known to have a threshold of sensitivity of 10 nanograms per mm3 of antigen X, then spot 10 would ideally have such a concentration. Spots 11 and 12 would have progressively increasing concentrations (e.g., 30 ng/mm3 and 90 ng/mm3, respectively). Spots 9 and 8 would have progressively decreasing concentrations (3 and 1 ng/mm3). Spot 7 is designed to test specificity rather than sensitivity. Therefore, spot 7 would comprise an irrelevant antigen (antigen Y) immobilized onto the membrane matrix. Ideally, the concentration of antigen Y in spot 7 will be higher than the threshold concentration for detecting antigen X (10 ng/mm3).

Figure 3:
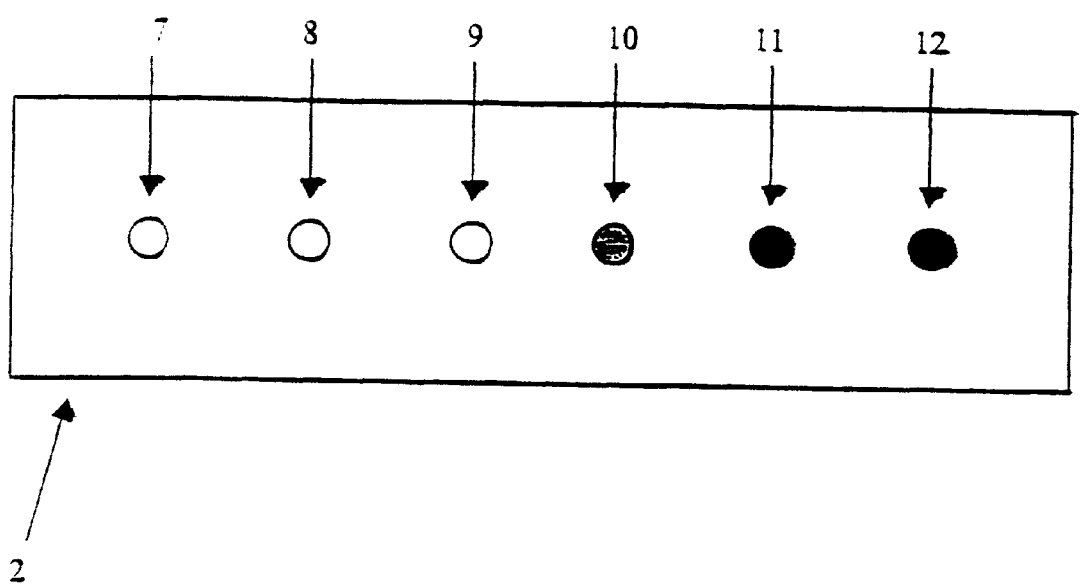
FIG. 3 is an face view of the antigen strip showing the degree of color development after a representative immunohistochemical assay.

FIG. 3 demonstrates the expected colorimetric result of the antigen spots after an immunohistochemical assay. The assay sensitivity and peptide concentrations are as stated in the above paragraph. Spots 10–12 are increasingly dark colored, owing to the increasing concentrations of peptide antigen. Spots 8 and 9 are colorless, since their concentration is stated to be below the level of detection. Spot 7 is colorless, since the antibody to antigen X does not bind to antigen Y (comprising spot 7).

MATRIX

The quality control reagent moieties are affixed to a matrix or membrane as described herein. The matrix can be manufactured of materials capable of binding macromolecules. Suitable matrix materials include nylon, nitrocellulose, and polyvinylidenedifluoride (PVDF). Nitrocellulose is commonly used for Western (protein), Northern (RNA) and Southern (DNA) blots, and is capable of binding macromolecules through non-covalent bonds. PVDF and nylon have greater tensile strength than nitrocellulose and can be derivatized to allow covalent coupling of macromolecules. Such matrices are commercially available and sold as IMMOBILON® AV (Millipore Corporation, Bedford, Mass.) or Immunodyne membrane (Pall Corporation, East Hills, N.Y.). Both matrices are derivatized by the manufacturer so that there is an abundance of free carboxyl groups on their surface. This allows for the coupling of macromolecules to the carboxyl groups through an amine or a sulfhydryl group.

Macromolecules are coupled to the matrix in the present invention by placing a small aliquot (less than ten microliters) of the macromolecule-containing solution on top of the activated matrix. The macromolecule, such as the antigen or peptide, is dissolved in a coupling buffer. The coupling buffer is preferably at a pH that maximizes the reaction of the macromolecule to the derivatized matrix. A preferred buffer is 0.5 M Potassium phosphate pH 7.4. The reaction is performed at room temperature. One hour is a preferred period of time for coupling, for convenience of manufacture and typically results in approximately 80% coupling efficiency. The matrix is then rinsed with buffer to remove any unbound macromolecules.

The matrix is spotted with a series of dilutions of the relevant target molecule or target molecule mimic (e.g., synthetic peptide antigen). Different concentrations of the antigen (peptide), will be useful in quickly estimating the extent of colorimetric development without the need for microscopic examination. For example, the synthetic peptide control concentrations can be appropriately calibrated so that a 3+ control reaction will yield a strong tissue signal with minimal background. The amount of antigen blotted onto the matrix would need to approximate the amount of antigen present in the tissue section. This can be empirically determined by coupling sufficient antigen to the matrix so that the color development on the matrix approximately parallels the intensity of the color development in the tissue section itself.

Typically, the first spot is the antigen at the highest concentration, and is expected to yield a strong positive reaction (e.g., detectable signal) after IHC staining. Subsequent serial dilutions vary from two to twenty fold in concentration. It is desirable to have a clearly defined limit of sensitivity. Specifically, the user of this control strip should be able to view the immunologic reactions that occur on the strip, and unequivocally identify an endpoint of sensitivity. The colorimetric IHC reaction product is strong above the limit of sensitivity and significantly weaker or absent below it. Therefore, the antigen dilutions are sufficiently different from each other so that there is a sharp falloff in immunoreactivity, creating a clearly-defined limit of sensitivity. A preferred embodiment of the invention is to spot the series of dots with antigen at approximately 3–6 fold serial antigen dilutions. An irrelevant antigen of similar size and charge characteristics is also spotted at the end of the strip. The irrelevant antigen provides a control for specificity of the immunologic reaction.

Additionally, a semi-quantitative determination of the concentration of a target molecule in a biological sample can be ascertained by comparing the detectable signal (e.g., color) generated from the antigen present in the biological sample and the detectable signal generated from the antigen in the quality control reagent moiety. The closest match of detectable signals between the sample and the control is indicative of the approximate concentration of the antigen in the sample.

The relevant antigens are spotted on the matrix surface using micropipettes or precision syringes. This can be accomplished in an automated fashion using an array of micropipettes that repetitively apply a defined number of microliters to defined positions on the quality control strips (matrix).

An alternative embodiment of the invention is to place multiple, distinct antigens onto the matrix. In this alternative, a single quality control device might have all of the relevant antigens for a particular disease state. For example, one device might be for a lymphoma IHC panel and contain antigens for many of the relevant antigens for a lymphoma diagnostic work up. Another device can be for a soft tissue tumor IHC panel, another for an undifferentiated "round, blue-cell" tumor work up, etc. In this fashion, the synthetic control devices are more broadly applicable to many different monoclonal primary antibodies.

After the coupling procedure, the derivatized matrix still contains a high density of available carboxyl groups for coupling to macromolecules. According to one manufacturer (Millipore Corporation, Bedford, Mass.), a carboxyl group is present every seven Angstroms on the matrix. Therefore, only a small proportion of the active carboxyl sites on the matrix are typically occupied by a macromolecule after coupling. The remaining carboxyl groups must be "quenched" (or "capped"), blocking any future potential reactivity. The matrix is quenched with any of a variety of small molecules that have free amino groups. Suitable quenching agents include ethanolamine, ethylenediamine, dithiothreitol, aminoethanediol, and aminopropanesulfonate. Alternatively, proteins such as gelatin or casein or amino acids such as glycine, can quench the matrix. A recommended quenching procedure is to cover the membrane with 10% v/v monoethanolamine in 1.0 M Sodium Bicarbonate buffer, pH 9.5. The matrix is incubated with the quenching solution for two hours at room temperature with constant agitation. The quenching solution is then aspirated and the matrix rinsed with 0.01 M Sodium Phosphate, 0.14 M NaCl, pH 7.4, 0.1% v/v Tween 20 (PBS-Tween). Each wash is for 30 minutes with constant agitation. The wash solution is then aspirated, and the matrix is allowed to dry.

ANTIGEN

Two forms of antigen can be used as a synthetic positive tissue control. First, the whole antigen can be coupled to the membrane. A list of some of the most commonly used antigens for clinical IHC diagnosis is shown in Table 1. Some of these antigens are available commercially. Examples include human immunoglobulins, prostate specific antigen, S-100 antigen, alpha-fetoprotein, and carcinoembryonic antigen, available from Fitzgerald Industries International, Inc., Concord, Mass. Other antigens can be isolated by solubilization of cultured cells or tissue homogenates and purification by affinity chromatography. Affinity purification methods are well known to those skilled in the art.

Antigens can also be obtained by recombinant DNA methods. cDNA constructs encoding the desired antigen can be transfected into suitable host cells, expressed and purified using techniques well-known to those of skill in the art.

Alternatively, a short peptide can serve as the antigen. Suitable peptides are typically approximately ten amino acids in length, but can be longer or shorter in length and still specifically bind antibody. Antibodies only bind to a small region of an antigen, typically comprising a few amino acids. Antibody epitopes of protein antigens can be broadly classified as sequential ("linear") or conformational ("discontinuous"). This classification is based on whether or not the amino acids that interact with the antibody are positioned immediately adjacent to each other in the linear amino acid sequence of the native protein. The surface of the antigen that interacts with the antibody can thus either consist of amino acids that are adjacent to each other or of amino acids that are separated in the primary sequence but brought together as a result of the natural folding of the protein to its native shape. Epitopes consisting of residues close together in the primary sequence are called linear, continuous, or sequential epitopes, whereas epitopes consisting of residues separated in the primary sequence are called discontinuous or conformational epitopes.

Short peptides can substitute for antigens when monoclonal antibodies are used. Monoclonal antibodies have a single, defined binding epitope. Different monoclonal antibodies often bind to distinct epitopes of an antigen. Therefore, when short peptides are used as antigens in the synthetic positive control device, they are specific to the monoclonal antibody that is being used. Each monoclonal antibody requires a distinct peptide sequence as a surrogate antigen. Therefore, the synthetic positive controls, using short peptides as antigen, are both antigen-specific as well as antibody-specific.

Several of the relevant peptides for antigens in Table 1 have been identified for specific monoclonal antibodies. For example, the 20 amino acid tandem repeat in the extracellular domain of polymorphic epithelial mucin (cancer-- associated antigen CA15-3) is shown below, each letter representing an amino acid.

TABLE 1

COMMON ANTIGEN TARGETS FOR CLINICAL IHC ASSAYS

PROGNOSTIC MARKERS

Estrogen receptor
Progesterone receptor
p53 protein
Ki-67 protein
Proliferating cell nuclear antigen (PCNA)
HEMATOLOGIC MARKERS CD3
CD15
CD20
CD30
CD34
CD45
CD45RO
CD99
Kappa light chain
Lambda light chain
Factor VIII
EPITHELIAL DIFFERENTIATION MARKERS Prostate specific antigen (PSA)
Prostate specific alkaline phosphatase (PSAP)
Cytokeratin
Epithelial membrane antigen (EMA)
Carcinoembryonic antigen (CEA)
Polymorphic epithelial mucin
Mesenchymal differentiation markers
Desmin
Vimentin
Actin
Collagen type IV
MELANOCYTIC MARKERS

S-100
HMB45
MISCELLANEOUS

Neuron-specific enolase
Glial fibrillary acidic protein
Chromogranin
Synaptophysin The binding sites for the DF3 (DAKO Corporation, Carpinteria, Calif.) and B27.29 monoclonal antibodies are shown above and below the sequence SEQ ID NO:1. The relevant region is indicated by the dotted lines. (Reference: Bon GG, von Mensdorff-Pouilly S, Kenemans P, van Kamp G J, et.al. Clinical and technical evaluation of ACS BR serum assay of MUCI gene-derived glycoprotein in breast cancer, and comparison with CA15-3 assays. Clin. Chem. 1997 43:585–593).

```
        --------DF3-----
   -P A H G V T S A P D T R P A P G S T A P-
           ----B27.29-------
```

Two general methods for identifying relevant peptides are known to those skilled in the art. One of these methods is the use of fragments of the protein antigen that are identical to one or more portions of the linear sequence. Sequence mapping technologies such as Multipin Peptide Synthesis Technology (Chiron Mimotopes, Victoria, Australia) enable linear sequence mapping by creating overlapping series of peptides on a 96 pin plastic structure. In this method, the primary sequence of the protein must be known. Using automated peptide synthesis equipment, overlapping fragments of the protein are synthesized on the various pins. For example, pin #1 might have the first ten amino acids. Pin #2 would have amino acids 2–11, pin #3 amino acids 3–12, etc. If the monoclonal antibody recognizes a linear epitope, then it will probably recognize and bind to one or more of the protein fragments on the pins.

From general experience with peptide mapping, only approximately 5–10% of monoclonal antibodies bind to linear epitopes. The remaining epitopes are conformational (discontinuous). Therefore, an alternative method of identifying antibody-binding peptides is required. To identify discontinuous epitopes, the preferred method of peptide identification is known as phage display. Phage display, the display of genetically encoded diversity on the surface of M13 filamentous bacteriophage, allows the production and screening of tens of millions of proteins and peptides in a few weeks (Ladner, R. and S. Guterman, in WO90/02809 (1990), the teachings of which are herein incorporated in their entirety by reference.; Ladner, R., et al., Directed Evolution of Novel Binding Proteins, (1993) U.S.; Wells, J. and H. Lowman, Curr. Op. Struct. Biol., (1992) 3(4): p.355–362) (McLafferty, M., et al., Gene, (1993)) 128:p.29–36; Clackson, T. and J. Wells, TIBTECH, (1994) 12: p. 173–184), the teachings of which are herein incorporated in their entirety by reference. The organisms containing those peptides that have the desired binding characteristics can be replicated, allowing repeated screening with increased stringency and amplification of the ligands. After a few rounds of screening and amplification, the peptides that remain are the higher affinity binders to the target molecule. Phage display is recognized as an efficient method of producing proteins and peptides that bind to targets of interest. (Ladner, R. and S. Guterman, in International patent application WO90/02809 (1990); Ladner, R., et al., Directed Evolution of Novel Binding, Proteins, (1993) U.S.; Roberts, B., et al., Proc. Natl. Acad. Sei. USA, (1992) 89: p. 2429–2433; Markland, W., A. Ley, and R. Ladner, Biochemistry, (1996) 35: p. 8058–67; Markland, W., et al., Biochemistry, (1996) 3)5: p. 8045–57; Ley, A., W. Markland, and R. Ladner, Mol Divers, (1996) 2: p. 119–24, the teachings of which are herein incorporated in their entirety by reference.

Adhesive Babking

A preferred embodiment for the synthetic antigen control strips is that they peel off from an 8.5×11 inch sheet. Each sheet would contain a plurality of control strips. The user simply peels off the appropriate antigen control from the sheet and applies it to the end of the slide, Therefore, the patient's name and identifying information would be at one end of the slide, and the antigen control at the other. Each strip would be spotted with several different concentrations of antigen.

Commercially available nylon or PVDF membranes can be used to create adhesive strips using techniques established in the printing industry. Specifically, a pressure-sensitive adhesive is applied to the back of the membrane. A suitable adhesive is FASSON S727 acrylic adhesive, because it is waterproof and permanent. Backing paper is then applied to the adhesive-coated nylon membrane. A suitable backing paper is 50 pound Kraft paper with a silicone liner. The purpose of the backing and liner is to provide a surface from which the membrane strips can be peeled. When the membrane strips are peeled away from the backing, the adhesive largely remains with the membrane. The application of adhesive and backing paper is typically performed by machinery that starts with two rolls (one roll of nylon membrane and backing paper, each) and ends with one roll of the nylon-adhesive-backing paper sandwich.

An alternative method of fabricating a membrane with an adhesive backing is to apply a double-faced tape to the back of the membrane. The double-faced tape comprises a film with adhesive coatings on both sides. A release liner covers the adhesive on one side and the other adhesive side is applied to the back of the membrane. Suitable double-sided tape can be obtained commercially, such as from Adhesives Research, Inc., Glen Rock, Pa. Suitable tapes generally use acrylic adhesives and polyester films. Acrylic adhesives are preferred because they exhibit a high degree of solvent resistance and are biologically inert. Examples of suitable tapes include their model Arcare® 7737, 8570, 7840, and 7841. The membrane and double-sided tape are applied to each other by machinery well known in the printing and labels industry, where each starts out as a separate roll. Each spool feeds its film or membrane into a roller that compresses the tape against the membrane. The hybrid sandwich of membrane and tape is then taken up on a third spool.

Use of the Quality Control Device

In practice, the technologist typically mounts a tissue section, cytospin, or cellular smear on a glass microscope slide so that the stained specimen can be visualized with a microscope. These techniques are well-known to those of skill in the art. The quality control strip is applied to the same glass slide, near or adjacent to the specimen. In this manner, the strip receives the same series of reagents, for the same incubation times, temperatures, and washing conditions as the biologic specimen. For immunohistochemical assays, a series of antibodies are applied to a biologic sample, such as a tumor section. The first antibody is for the purpose of conveying the assay specificity. A list of many commonly used antibody targets is listed in Table 1. Typically, the antibodies will be monoclonal, of murine origin. The primary antibody is commonly incubated with the tissue section for a period of about 15–60 minutes.

The remaining reagents in the assay are considered detection reagents. They demonstrate where in the biologic specimen the first (primary) antibody bound, by causing that site to become colored. After the primary antibody incubation, the slide is rinsed with a buffer, commonly phosphate buffered saline, in order to remove any unbound antibody molecules from the surface of the slide. Then, a secondary antibody is applied. A common secondary antibody is a polyclonal anti-murine IgG or IgM recognizing unique epitopes present on murine immunoglobulins. This secondary antibody is commonly coupled (covalently) with biotin. Consequently, wherever the primary antibody bound to the biologic specimen, biotin molecules are now found. After the secondary antibody incubation, excess unbound antibody reagent is rinsed off with a buffer. The third step in the reaction sequence provides for coupling of an enzyme, typically peroxidase, to the site where the primary antibody bound. This is commonly performed by incubating the slide with avidin (or streptavidin) covalently coupled to peroxidase. Avidin (and streptavidin) has a high binding affinity to biotin. Therefore, peroxidase will be immobilized at sites of biotin. After completion of this third step in the reaction, the excess unbound enzyme—avidin reagent is rinsed off with buffer. The final step is the addition of an enzyme substrate. Substrates are chosen so that they are soluble and relatively colorless. However, after action of the enzyme upon the substrate, they become colored and insoluble. Therefore, the substrate precipitates wherever the enzyme is found. A commonly used peroxidase substrate is 3,3-diaminobenzidine.

Numerous other variations of the immunohistochemistry procedure exist and are described in the relevant literature. This quality control strip is designed so that it will serve as a positive control regardless of the detection system used. Whatever series of reactions that occur on the biologic sample will also occur on the quality control strip. The use of more sensitive detection systems will correspondingly be reflected in the increased color intensity of both the biologic sample and the quality control strip. Moreover, a more sensitive detection system will detect the lower concentration spots of antigen. The opposite will be true of less sensitive detection methods. In this manner, the quality control strips can verify and quantify the performance characteristics of immunohistochemical assays.

Although immunohistochemical assays have been specifically referenced in the examples, the same quality control method can also be applied to other types of assays performed on microscope slides. For example, nucleic acid targets can be immobilized onto the matrix and serve as positive controls for assays such as iii sitii hybridization. In this configuration, probes that detect specific nucleic acid sequences will also hybridize with complementary sequences on the quality control strip. Such assays are well known to practitioners in the field and published in scientific literature. Commonly performed in situ hybridization assays test for the presence of viruses. As a control, dsDNA containing the desired double-stranded sequence is covalently coupled to the matrix. A convenient method for coupling dsDNA is to derivatize it at one end with a free amino group. The free amino group can then be coupled to the carboxy-derivatized matrix in the same fashion as already described.

This quality control method can also be applied to the field of histochemical stains. Classes of compounds that are detected by histochemical methods can be immobilized onto the matrix. Examples include carbohydrates for the Periodic acid-Scheff (PAS) stain, mucins for the mucicarmine stain, extracellular matrix components for the reticulin stain, etc.

With respect to the five criteria previously mentioned, the quality control devices described herein are antigen-specific, easily manufactured in large quantities, inexpensive, stable and standardized. The antigenic specificity is conferred by virtue of the peptide that is immobilized onto the antigen strip. Short peptides (e.g., approximately 10 amino acids long) are easily manufactured at low cost. Moreover, they tend to be quite stable, especially if stored at 4° C. By applying a calibrated amount of peptide to the strip, under reproducible coupling conditions, the amount of peptide bound can be standardized.

The synthetic controls described herein provide an absolute quantitative standard for immunohistochemical reactions. The antigen strips are manufactured so that a series of known concentrations of peptide are deposited, as previously described. This provides laboratories the means to verify that they each have comparable assay sensitivity. For example, estrogen receptor analysis is commonly performed by visually quantifying (under microscopic examination) the percentage of tumor cells that stain positively using an antibody to estrogen receptor. However, a significantly more sensitive assay will be expected to detect more positive cells than a less sensitive assay. Therefore, assay sensitivity standardization is important for laboratories to meaningfully communicate their results. Since the synthetic antigen control strips are manufactured in a standardized and reproducible fashion, each laboratory has a reproducible assay standard.

In summary, the quality control strips can serve three functions:

1. VALIDATION OF PROPER ASSAY PERFORMANCE.

The strips contain analytes that are identical to or mimic the proteins, peptides, nucleic acids, carbohydrates, lipids, etc. found in the cell or tissue sample that is being analyzed. These analytes produce a substantially similar colorimetric signal as the signal produced by the staining reaction on the cells or tissue section. Therefore, if the quality control strip yields a positive signal, it serves as an indicator that the staining procedure was performed correctly. This is particularly useful in instances where the analytes being tested for in the cell or tissue sample are not present, e.g,. it is useful in assays that produce a negative tissue reaction. A positive reaction on the quality control strip establishes that the negative result in the tissue sample is a true negative rather than being due to errors in the staining procedure.

2. DETERMINATION OF ASSAY SENSITIVITY.

The strips that contain varying quantities of the analytes provide a method for establishing the endpoint of sensitivity of the assay, e.g., the lowest detectable concentration of analyte on the control strip that is detectable represents the threshold of sensitivity.

3. QUANTITATION OF ANALYTES IN THE CELL OR TISSUE SAMPLE.

The strips that contain varying quantities of the analytes can provide a concentration reference standard that can be used for analyte quantification. Specifically, the colorimetric signals can be expected to vary according to the analyte concentration. Low analyte concentrations will yield weak calorimetric signals; high concentrations will yield strong calorimetric signals. The intensity of the signal can either be estimated visually or directly quantified using computer-assisted image analysis techniques. With either method of quantification, the signal intensity on the quality control strip can be correlated with the signal intensity found in the tissue section. In this manner, the approximate amount of analyte in the cell or tissue section can be estimated. If quantitative signal measurement methods are used (image cytometry), then a calibration curve can be established every time the assay is run using the quality control strip, e.g., the signal intensity is plotted (y axis) against the analyte concentration (x axis). The signal intensity in the cells or tissue section can then be interpolated on this graph to deduce the analyte concentration.

While this invention has been particularly shown and described with references to preferred embodiments thereof, it will be understood by those skilled in the art that various changes in form and details may be made therein without departing from the spirit and scope of the invention as defined by the appended claims.

EXEMPLIFICATION: EXPERIMENTAL DESIGN AND METHODS

1. SELECT PHAGE THAT MIMIC TARGET EPITOPES FROM MONOCLONAL ANTIBODIES COMMONLY USED IN CLINICAL IMMUNOHISTOCHEMICAL LABORATORIES.

For the device and methods describe herein, it is desirable to identify peptides that will mimic the antigen-specific interaction of antibody with the native antigen. Suitable peptide sequences identified as described herein are more amenable to consistent manufacture than the native protein itself. The monoclonal antibody clones suitable for use as described herein are those that recognize the antigen even after the tissue has been fixed with formalin and embedded in paraffin wax. These monoclonal antibody clones represent some of the most commonly used primary antibodies in the clinical IHC laboratory. A phage library that is suitable for use is a random 10-mer peptide library, inserted into the Gene 3 phage protein, available from Dyax Corp., Cambridge, Mass.

(a) SCREENING OF PEPTIDE AND PROTEIN DISPLAY LIBRARIES.

The following procedure is used to select phage from libraries that bind specifically to antibody combining sites. Selection of phage is effected through binding of phage to a biotin-conjugated target antibody with subsequent capture on streptavidin-coated beads.

Antibodies are biotin-conjugated using the commercially available NHS-biotin reagent (NHS, for N-hydroxysuccinimide, Vector Laboratories, Burlingame, Calif.). The reaction is carried out in 100 mM borate buffer, pH 8.0, for 4 hours at room temperature. Success of the biotin conjugation is measured by testing for capture of an aliquot of antibody by streptavidin beads. If the antibody has been successfully conjugated, there will be a disappearance of protein from the column effluent. Moreover, the column effluent will be devoid of staining capability. Following the reaction, the antibody is dialyzed against several changes of PBS overnight.

The biotin-conjugated antibody is then diluted to 4 $\mu$g/ml in phosphate-buffered saline (PBS), and 1 $\mu$g of the antibody is combined with $10^{11}$ phage particles in a volume of 1 ml of PBS containing 4% blotto and 0.05% Tween 20. Binding is allowed to occur at 25° C. for 1 hour, while rotating on a nutating agitator.

To avoid isolation of phage that recognize streptavidin, some researchers have found that alternating the bead types in sequential rounds of phage selection works well. Another method is to add excess biotin as a competitor to the solution after the phage have been captured, to avoid capturing phage that bind to the biotin binding site (McLafferty, M., et al., Gene, (1993) 128:p.29–36).

Capture of bound phage is effected by adding 100 $\mu$L of streptavidin-coated magnetic beads (Dynal Corp.) that have been pre-blocked in the PBS/blotto/Tween-20 buffer, and incubating, with end-over-end rotation for 30 minutes. The beads are retained with a magnetic chamber during washing with blocking buffer (5 times) and with PBS (5 times) to remove non-bound and weakly bound phage. Bound phage are eluted by dropping the pH to 2 by addition of 150 $\mu$L 50 mM glycine-HCl to the bead pellet and incubating for 15 minutes at 25° C. The acid-eluted phage are neutralized by addition of 150 $\mu$L of 200 mM NaPO$_4$ buffer, pH 7.5 and are amplified for further rounds of screening From section (a), pools of phage clones are obtained that bind specifically to each of the target antibody molecules.

(b) ENRICHMENT FOR CLONES THAT CONTAIN HIGH AFFINITY BINDERS TO TARGET ANTIBODY.

OVERVIEW:

The phage libraries contain between $10^8$–$10^9$ distinct phage particles. At the outset, there are approximately 100–1000 copies of each phage particle. Therefore, there are a total of approximately $10^{10}$–$10^{11}$ phage particles in the first screen. The goal of enrichment is to select only those phage particles that bind specifically and with high affinity to the target antibody. Typically, between $10^5$–$10^6$ binding phage are recovered during the first round of screening. Many of the phage often represent redundant particles.

This pool of phage is then amplified and further screened. The enriched phage library is much less complex than at the outset, since this second round is pre-selected for binding phage. Therefore, the fraction of binding phage is usually to be greater than in the first round. Since this second round of amplification starts with the same number of total phage (after amplification of the first round of selected phage), up to $10^7$–$10^8$ phage particles are expected to be obtained after the second round. Each round of screening should yield a greater number of binding phage, indicating enrichment. When the number of phage recovered has leveled off, this is an indicator that no further enrichment is occurring.

The eluted phage are used to inoculate 5 ml of a 1:100 dilution of an overnight culture of TG1 Ecoli in 2× YT media, which are then grown for no more than 8 hours at 37° C., shaking at 220 rpm. The cells are pelleted by centrifugation at 5000 rpm in a Sorvall Superspeed T21 tabletop centrifuge, and the phage in the supernatant are recovered by precipitation with polyethylene glycol. The selection is then repeated. Four rounds of selection are usually sufficient to enrich the pool for phage that contain high affinity binders to the antibody. For increased selection pressure, the stringency conditions for binding phage can be increased (e.g., by increasing the salt concentration or adding non-ionic detergent).

From section (b), it is expected to obtain between 10 to 12 phage clones that exhibit high affinity binding, to each of the target antibody molecules. Some of these phage will be identical to each other. Ultimately, the aim is to generate approximately five distinct peptide sequences that bind to the antibody. Each of these clones are amplified and sequenced so that peptides can be generated using solid phase chemical synthesis.

(c) PHAGE CLONE AMPLIFICATION, SEQUENCE IDENTIFICATION AND PEPTIDE PRODUCTION

Large quantities of each of the selected phage are grown and nucleic acid extracted for sequence analysis. Based on the nucleotide sequence coding for the inserted ten-mer peptide, corresponding peptides are synthesized. Numerous commercial vendors provide peptide synthesis capabilities. The binding affinity of each of the selected peptide sequences for their antibodies is determined using Scatchard analysis. The specificity of binding for each peptide antigen mimic is tested using irrelevant, isotype-matched antibodies.

At the end of the above process, peptide antigens are identified that mimic the binding, characteristics of the monoclonal antibody to the real antigen.

2. PEPTIDE (ANTIGEN MIMIC)—MATRIX OPTIMIZATION (a) OVERVIEW

Once an appropriate peptide sequence is identified, the next step is to determine the linear range of the peptide concentration on the control strips. In other words, how much peptide should be placed onto the nylon strip so as to be most sensitive to early reagent failure?

Carboxy-derivatized nylon or PVDF matrices allow high capacity covalent immobilization of proteins to the surface of the matrix while retaining biological activity. Processing steps include the covalent binding of protein to the membrane and a blocking step to quench the remaining covalent binding capacity, as described herein. Since proteins are covalently bound to the membrane, standardization is more readily achieved than with matrices that non-covalently adsorb proteins, such as nitrocellulose. Other desirable characteristics of nylon or PVDF membranes include moderate cost, resistance to microbial attack, and mechanical strength.

(b) MAXIMIZING SENSITIVITY TO EARLY REAGENT FAILURE.

Described herein is a preferred method for determining the optimal concentration of peptide on the quality control strip. Based on the manufacturers' specifications (Millipore Immobilon-AV Affinity Membrane or Pall Biodyne D membrane), the coupling capacity far exceeds the likely desired peptide concentration. In order to serve as a useful absolute quantitative standard, it is important to precisely control the amount of peptide that is bound to the membrane.

Different laboratories use slightly different concentrations of primary antibody, depending upon the sensitivity of their detection systems. If the purpose of the control strip is to monitor assay sensitivity, then this invention will be configured to bracket a range of peptide concentrations. A series of two to five-fold dilutions for spots of peptide on a single control strip is ideal. The control strip will include a spot with an irrelevant peptide. If the control strips are configured with a series of peptides at the correct concentrations, then they will be highly sensitive to a decrement in antibody activity. To achieve maximal sensitivity, it is important to identify the dynamic (linear) range for the IHC assay for each peptide/primary antibody combination.

For each peptide/primary antibody combination, dynamic ranges are determined as follows. A series of spots are placed onto a derivatized matrix. Each spot represents a two to five fold dilution of peptide, so that the peptide concentration varies over a broad range. Based on prior experience with IHC assays, that the maximum amount of peptide in a 1 $\mu$l spot that will likely be needed is 5 ng. The actual dynamic (linear) range may be much lower, possibly in the picogram range.

Figure 4:
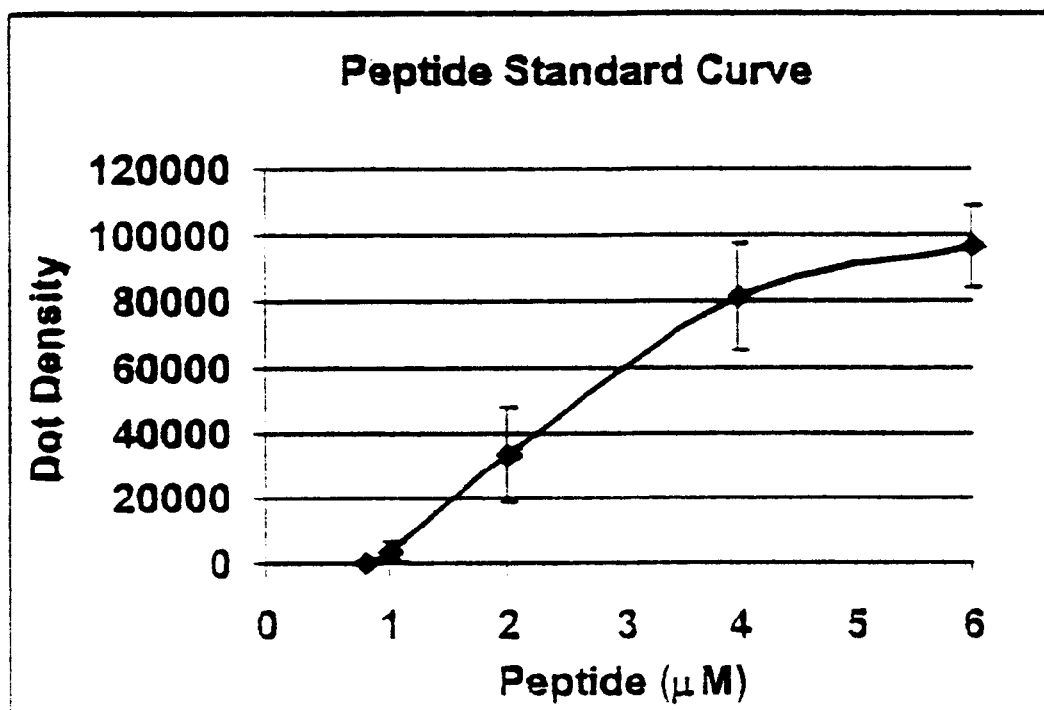
FIG. 4 is a graphic representation of an experiment to determine linear assay range.

The spots are then detected using primary antibody concentrations already optimized for tissue IHC staining. Typically, primary antibodies in IHC assays are used at a 1–10 $\mu$g/ml concentration. The intensity of the spots will be estimated on a 1–4+ scale. The data are be plotted as demonstrated in FIG. 4 (the x and y axis numbers are completely arbitrary in the example). The ideal mean peptide concentration for the center spot on the control strip is that concentration near the juncture of the linear and plateau portions of the graph. It is at this peptide concentration that the control strips of the present invention will be most able to detect early reagent failure. If a reagent begins to experience diminished activity, the colorimetric intensity (y axis) will correspondingly diminish (linear portion of curve). On the other hand, operating on the plateau portion of the curve will cause a lack of colorimeric decrement if mild reagent degradation occurs.

3. VALIDATION OF SYNTHETIC CONTROL STRIPS

Each peptide mimic or antigen comprises a somewhat unique and independent product. Therefore, each needs to be independently validated. This section describes the process of validating the synthetic control strips to verify that (a) each synthetic control strip has a high signal to noise ratio, (b) the synthetic control strip is antibody-specific, and (c) each synthetic control stip is capable of detecting early reagent failure.

(a) MEASUREMENT OF THE SIGNAL TO NOISE RATIO

The synthetic control strip contains two distinct areas: (1) the reagent surface that is devoid of bound peptide, and (2) the test area with specific peptide. The test strip containing no peptide should be used as a test for non-specific binding of antibody to the membrane itself. Excessive background to the negative control (surface without peptide) indicates the need to investigate the blocking procedure, buffer composition, and/ or the washing procedure during the assay.

In order to conduct the validation, control strips can be generated with three portions, or regions, on the strip: (1) a portion that contains the relevant specific peptide, (2) a portion that contains an irrelevant peptide, and (3) a portion that does not contain any peptide. The latter two are both negative background controls. Each of the three regions are blocked and washed in an identical fashion. Namely, the strips are blocked in 4% blotto or 10 mg/ml casein) in PBS and washed with PBS with 0.05% Brij 35. The strips are then stained using a conventional immunostaining procedure.

At the end of the immunostaining procedure (but before the addition of the colorimetric substrate), the three sections of the control strip are separated from each other with a razor blade and placed into microtitre wells. A soluble peroxidase substrate is added to each well (o-phenylenedihydrochloride) with 0.3% $H_2O_2$. After the color develops, the strips are removed from the wells with a forceps. Color development is measured spectrophotometrically with a microtitre plate spectrophotometer. A signal to noise ratio is then calculated. The first portion of the strip (relevant peptide) represents the signal. The other two portions are both negative controls. A S/N ratio greater than 10 should be obtained for acceptable performance.

(b) TESTING FOR NON-SPECIFIC BINDING OF PEPTIDES TO OTHER ANTIBODIES

Before settling upon a specific candidate peptide for use as an antigen mimic, it is important to verify that it binds only to the desired antibody. Therefore, it is desirable to test the peptide against an array of 5–10 different primary antibodies. The experimental method is nearly identical to that described above, for determining the signal to noise ratio. Namely, replicate spots of the peptide sequence are coupled onto a matrix (by methods previously described). The spots are separated from each other and placed into microtitre wells, as previously described. Different primary antibodies, each at the appropriate working concentration (usually 1–10 micrograms/ml), are added to the wells. In this manner, the same peptide target is tested against a variety of different primary antibodies. After incubation and removal of the primary antibodies, the remainder of the detection procedure is carried out. An antigen-specific mimic causes a colormetric reaction to occur following incubation with the specific antibody but not by other non-specific primary antibodies.

(c) VALIDATING SENSITIVITY OF THE CONTROL STRIPS TO DETECTING EARLY REAGENT FAILURE

For optimal performance, the range of concentrations of antigen or peptide mimic (coupled onto the matrix) should be such that it will be most useful in detecting early decrements in reagent performance. This is in contradistinction to standard tissue controls in that the amount of an analyte in a tissue control can not be varied at will. The control strip is most sensitive to detecting early reagent failure when the amount of antigen or antigen mimic on the strip brackets the threshold of detection.

To test the control strips, reagent failure is simulated in a typical immunohistochemical staining procedure. This is accomplished by serially diluting the primary antibody. The limit of sensitivity is measured by visually noting the lowest peptide concentration that will yield a 1+ colorimetric signal. This type of visual quantitation is similar to that used for hemagglutination reactions. The intensity of the reaction (1–4+) is graphed against the concentration of the primary antibody. The goal is to identify the smallest increment in primary antibody dilution that can be detected using the control strips. The sensitivity of the controls strips is quantified as the smallest increment (change in concentration) in primary antibody dilution that can be reliably detected. (See, for example, Table 2.)

TABLE 2

| Primary antibody concentration | Colorimetric intensity |
| --- | --- |
| 40 μg/ml | 4+ |
| 20 μg/ml | 4+ |
| 10 μg/ml | 4+ |
| 5 μg/ml | 3+ |
| 2.5 μg/ml | 2+ |
| 1.0 μg/ml | 1+ |
| 0.6 μg/ml | 0 (negative result) |

In this example, the control strip is able to detect a two-fold dilution of primary antibody between 1 and 10 μg/ml of primary antibody.

Equivalents:

Those skilled in the art will recognize, or be able to ascertain using no more than routine experimentation, many equivalents to the specific embodiments of the invention described herein. Such equivalents are intended to be encompassed by the following claims.

---

We claim:

1. A quality control assay device comprising a matrix having a front surface and a back surface, wherein the front surface is a reagent surface comprising at least one quality control reagent moiety affixed to the matrix surface, and the back surface of the matrix is an adhesive surface, and wherein the adhesive surface of the matrix is affixed to a removable backing sheet and wherein the removable baking sheet is removed when an assay is performed on the device.

2. The device of claim 1 wherein the control reagent moiety is covalently affixed to the matrix.

3. The device of claim 1 wherein the matrix comprises a material selected from the group consisting of nylon, nitrocellulose and polyvinlyideneflouride.

4. The device of claim 1 wherein the reagent surface of the matrix comprises more than one control reagent moiety and wherein each moiety is spatially located in a discrete section of the reagent surface.

5. The device of claim 4 wherein each moiety comprises a different target molecule.

6. The device of claim 5 wherein the target molecule is selected from the group consisting of protein, polypeptide and nucleic acid.

7. The device of claim 5 wherein the assay is an immunocytochemical assay and the target molecule is detected with an antibody.

8. The device of claim 5 wherein the assay is an in situ hybridization assay and the target molecule is detected with a nucleic acid probe.

9. The device of claim 5 wherein the assay is a histochemical assay and the target molecule is reactive with a histochemical stain.

10. The device of claim 4 wherein each moiety comprises a different concentration of the same target molecule.

11. The device of claim 10 wherein the target molecule is selected from the group consisting of protein, polypeptide and nucleic acid.

12. The device of claim 10 wherein the assay is an immunocytochemical assay and the target molecule is detected with an antibody.

13. The device of claim 10 wherein the assay is an in situ hybridization assay and the target molecule is detected with a nucleic acid probe.

14. The device of claim 10 wherein the assay is a histochemical assay and the target molecule is reactive with a histochemical stain.

15. The device of claim 1 wherein the device is adhered to a microscope slide.

16. The device of claim 4 wherein at least one of the quality control moieties is a synthetic peptide.

17. The device of claim 1 wherein the adhesive surface comprises pressure-sensitive adhesive.

18. A method for determining the sensitivity of an assay for the detection of the presence or absence of one, or more, target molecules in a biological sample comprising the steps of:

a) providing a quality control device, wherein the quality control device comprises a matrix having a front surface and a back surface, wherein the front surface is a reagent surface comprising multiple quality control reagent moieties affixed to the matrix surface, wherein each moiety is spatially located in a discrete section of the reagent surface and each moiety comprises a different concentration of the same target molecule or target molecule mimic, and the back surface of the matrix is an adhesive surface, and wherein the adhesive surface of the matrix is affixed to a removable backing sheet;

b) removing the backing from the adhesive surface of the matrix and attaching the device to a flat, optically transparent surface;

c) performing the assay on the quality control device wherein the assay results in the detection of the target molecule; and d) determining the quality control moiety that contains the lowest concentration of said detectable target molecule or target molecule mimic, wherein determination of the lowest concentration of detectable target molecule or target molecule mimic is indicative of the sensitivity of the assay.

19. The method of claim 18 wherein the optically transparent surface is a microscope slide.

20. A method for validating the performance of an assay for detecting the presence or absence of a target molecule in a biological sample mounted on a flat, optically transparent surface, comprising the steps of:

a) providing a quality control device, wherein the quality control device comprises a matrix having a front surface and a back surface, wherein the front surface is a reagent surface comprising at least one quality control reagent moiety affixed to the matrix surface, wherein each moiety comprises a target molecule or target molecule mimic, wherein the back surface of the matrix is an adhesive surface and wherein the adhesive surface of the matrix is affixed to a removable backing sheet;

b) removing the backing from the adhesive surface of the matrix and attaching the device to the optically transparent surface;

c) simultaneously performing the assay on the biological sample and the quality control device, wherein the assay results in a detectable signal produced by the target molecule in the sample and the quality control reagent moiety; and d) detecting the signal, wherein detection of the signal produced by the quality control device is indicative of assay performance validation.

21. The method of claim 20 wherein the optically transparent surface is a microscope slide.

22. An assay method for the semi-quantitative determination of the concentration of a target molecule in a biological sample mounted on a flat, optically transparent surface, comprising the steps of:

a) providing a quality control device, wherein the quality control device comprises a matrix having a front surface and a back surface, wherein the front surface is a reagent surface comprising multiple quality control reagent moieties affixed to the matrix surface, wherein each moiety is spatially located in a discrete section of the reagent surface and each moiety comprises a different concentration of the same target molecule, or target molecule mimic, and wherein the back surface of the matrix is an adhesive surface, and wherein the adhesive surface of the matrix is affixed to a removable backing sheet; and b) removing the backing from the adhesive surface of the matrix and attaching the device to the flat, optically transparent surface;

c) simultaneously performing the assay on the biological sample and the quality control device, wherein the assay results in a detectable signal generated by the presence of the target molecule in the sample and the quality control moiety; and d) comparing the detectable signal generated from the target molecule in the biological sample with the detectable signal generated from the target molecule or target molecule mimic in the quality control reagent moiety to semi-quantitatively determine the concentration of target molecule in the tissue sample.

23. The method of claim 22 wherein the optically transparent surface is a microscope slide.

24. A quality control assay device for use in an assay that measures one or more analytes in a biological sample, wherein the biological sample is mounted on a flat, optically transparent surface, the quality control device comprises a matrix having a front surface and a back surface, wherein the front surface is a reagent surface comprising at least one quality control reagent moiety affixed to the matrix, wherein the quality control reagent moiety comprises one, or more, target molecules, or synthetic target molecule mimics, and the back surface comprises an adhesive surface which is affixed to a removable backing sheet and wherein the removable backing sheet is removed and the adhesive attaches the matrix to the flat, optically transparent surface to which the biological sample is mounted whereupon the assay is performed.

25. The device of claim 24 wherein at least one of the quality control moieties is a synthetic peptide.

26. The device of claim 24 wherein the flat, optically transparent surface is a microscope slide.

27. The device of claim 24 wherein the control reagent moiety is covalently affixed to the matrix.

28. The device of claim 24 wherein the matrix comprises a material selected from the group consisting of nylon, nitrocellulose and polyvinlyideneflouride.

29. The device of claim 24 wherein the reagent surface of the matrix comprises more than one control reagent moiety and wherein each moiety is spatially located in a discrete section of the reagent surface.

30. The device of claim 29 wherein each moiety comprises a different target molecule.

31. The device of claim 29 wherein each moiety comprises a different concentration of the same target molecule.

32. The device of claim 24 wherein the target molecule is selected from the group consisting of protein, polypeptide and nucleic acid.

33. The device of claim 24 wherein the assay is an immunocytochemical assay and the target molecule is detected with an antibody.

34. The device of claim 24 wherein the assay is an in situ hybridization assay and the target molecule is detected with a nucleic acid probe.

35. The device of claim 24 wherein the assay is a histochemical assay and the target molecule is reactive with a histochemical stain.

36. The device of claim 24 wherein the flat, optically transparent surface is a microscope slide.

37. A quality control assay device for use in an immunocytochemical assay for the detection of the presence or absence of multiple target molecules in cells or a tissue section, the device comprising a matrix having a front surface and a back surface, wherein the front surface is a reagent surface comprising multiple quality control reagent moieties affixed to the matrix, wherein each moiety is spatially located in a discrete section of the reagent surface, and the back surface of the matrix is an adhesive surface which is affixed to a removable backing sheet and wherein the removable backing sheet is removed and the adhesive attaches the matrix to the flat optically clear surface to which the cells or tissue section is mounted whereupon the assay is performed.

38. The device of claim 37 wherein at least one of the quality control moieties is a synthetic peptide.

39. The device of claim 37 wherein the control reagent moiety is covalently affixed to the matrix.

40. The device of claim 37 wherein the matrix comprises a material selected from the group consisting of nylon, nitrocellulose and polyvinlyideneflouride.

41. The device of claim 37 wherein the target molecule is selected from the group consisting of protein, polypeptide and or synthetic peptide.

42. The device of claim 37 wherein the target molecule is detected with an antibody.

* * * * *

UNITED STATES PATENT AND TRADEMARK OFFICE
CERTIFICATE OF CORRECTION

PATENT NO. : 6,281,004 B1  Page 1 of 1
DATED : August 28, 2001
INVENTOR(S) : Steven A. Bogen and Gail E. Radcliffe It is certified that error appears in the above-identified patent and that said Letters Patent is hereby corrected as shown below:

<u>Column 21, claim 1,</u>
Line 18, delete the word "baking" and substitute the word -- backing -- therefor.

Signed and Sealed this

Second Day of April, 2002

Attest:

JAMES E. ROGAN
*Attesting Officer*  *Director of the United States Patent and Trademark Office*

SEQUENCE LISTING

<160> NUMBER OF SEQ ID NOS: 1

<210> SEQ ID NO 1
<211> LENGTH: 20
<212> TYPE: PRT
<213> ORGANISM: Human

-continued

```
<400> SEQUENCE: 1

Pro Ala His Gly Val Thr Ser Ala Pro Asp Thr Arg Pro Ala Pro Gly
1               5                   10                  15

Ser Thr Ala Pro
            20
```